US012622638B2

(12) United States Patent
Rodgers

(10) Patent No.: US 12,622,638 B2
(45) Date of Patent: May 12, 2026

(54) CONFIGURING APPLICATIONS BASED ON A USER'S WAKEFULNESS STATE

(71) Applicant: Oracle International Corporation, Redwood Shores, CA (US)

(72) Inventor: Michael Patrick Rodgers, Lake Oswego, OR (US)

(73) Assignee: Oracle International Corporation, Redwood Shores, CA (US)

( * ) Notice: Subject to any disclaimer, the term of this patent is extended or adjusted under 35 U.S.C. 154(b) by 558 days.

(21) Appl. No.: 17/643,654

(22) Filed: Dec. 10, 2021

(65) Prior Publication Data

US 2023/0181100 A1      Jun. 15, 2023

(51) Int. Cl.
| | |
|---|---|
| *G16H 40/40* | (2018.01) |
| *A61B 5/00* | (2006.01) |
| *G06N 20/00* | (2019.01) |

(52) U.S. Cl.
CPC .......... *A61B 5/4809* (2013.01); *A61B 5/4812* (2013.01); *A61B 5/4815* (2013.01); *A61B 5/681* (2013.01); *A61B 5/7267* (2013.01); *G06N 20/00* (2019.01); *G16H 40/40* (2018.01)

(58) Field of Classification Search
CPC ... A61B 5/7267; A61B 5/7264; A61B 5/7275; A61B 5/4812; A61B 5/681; A61B 5/7282; A61B 5/02438; A61B 5/11; A61B 5/746; A61B 5/4809; A61B 5/486; A61B 5/4815; A61B 5/4806; A61B 5/1123; A61B 5/6801; A61B 5/6802; A61B 5/6824; A61B 5/6831; A61B 5/0024; A61B 5/6898; A61B 5/0004; A61B 5/316; A61B 5/6804; A61B 5/0082; A61B 5/332; A61B 5/00; A61B 5/256; A61N 1/0484

See application file for complete search history.

(56) References Cited

U.S. PATENT DOCUMENTS

| | | | |
|---|---|---|---|
| 2020/0289321 A1* | 9/2020 | Luo ...................... | A61B 5/4812 |
| 2020/0368491 A1* | 11/2020 | Poltorak .............. | A61N 1/0456 |

* cited by examiner

*Primary Examiner* — Deborah L Malamud
(74) *Attorney, Agent, or Firm* — Invoke

(57) ABSTRACT

Techniques for configuring one or more applications based on a detected wakefulness state of a user are disclosed. A system trains and applies a machine learning model to wakefulness data to compute a wakefulness state of a user. The system obtains the wakefulness data from wearable devices worn by the user and environmental devices in a user's environment. The system configures applications and/ or devices based on the computed wakefulness state of the user. The system configures the ability of devices or applications to generate visual, audible, or tactile notifications in response to determining that a user is awake or asleep.

26 Claims, 7 Drawing Sheets

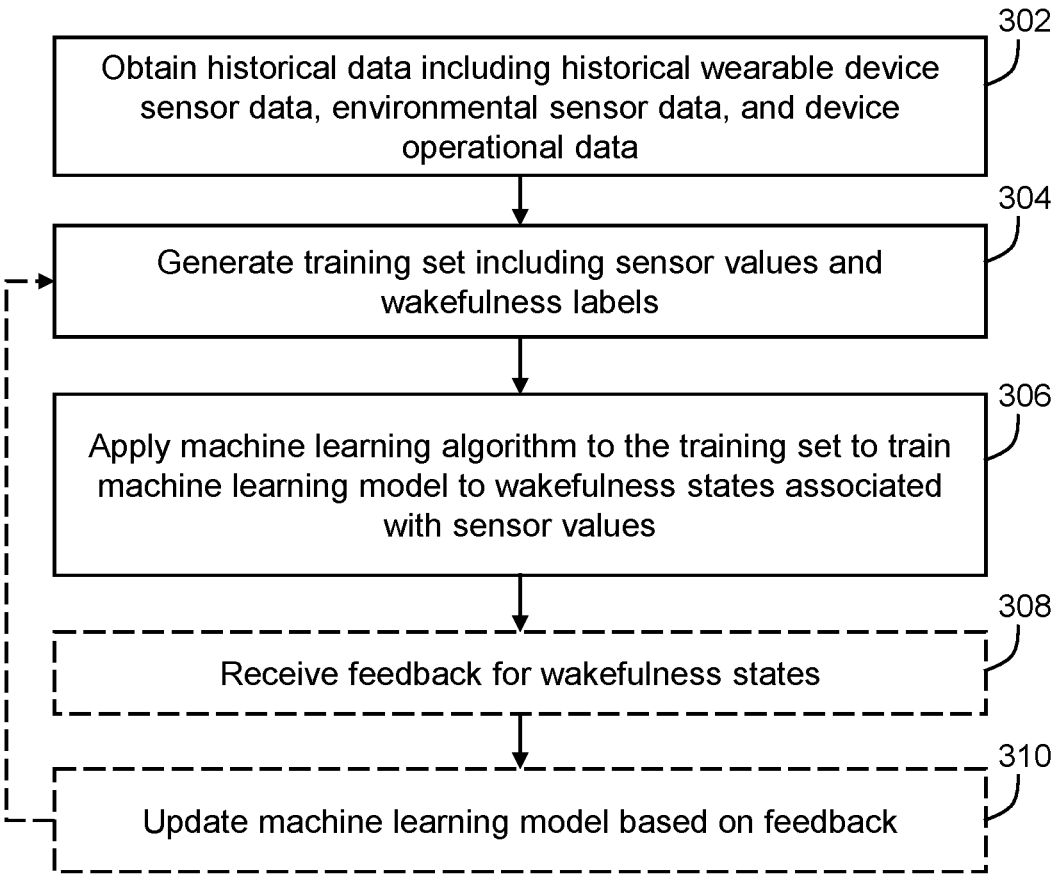

302

Obtain historical data including historical wearable device sensor data, environmental sensor data, and device operational data

304

Generate training set including sensor values and wakefulness labels

306

Apply machine learning algorithm to the training set to train machine learning model to wakefulness states associated with sensor values

308

Receive feedback for wakefulness states

310

Update machine learning model based on feedback

Fig. 3

CONFIGURING APPLICATIONS BASED ON A USER'S WAKEFULNESS STATE

TECHNICAL FIELD

The present disclosure relates to configuring one or more applications based on a detected wakefulness state of a user. In particular, the present disclosure relates to applying a machine learning model to a set of wakefulness state data to determine a wakefulness state and configure applications accordingly.

BACKGROUND

Wearable devices provide a wide variety of functionality for users, such as communications, media output, and monitoring physiological characteristics of the user. Wearable devices may use physiological characteristics to monitor a user's sleep. For example, a device may monitor the heart rate or movement of a user to determine a sleep state of the wearer. Some devices seek to improve a user's sleep quality by providing sleep information to the user once the user awakes. For example, a watch may detect the movement of the user during a period of time defined as sleep time by the user. The watch may communicate with a phone to inform the user whether the user had restless sleep or restful sleep based on the amount of motion detected by the watch. Other devices seek to improve the user's sleep while the user is sleeping by emitting relaxing sounds. For example, a watch may detect a heart rate of the user and alter sounds emitted by the watch based on the detected heart rate.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF THE DRAWINGS

The embodiments are illustrated by way of example and not by way of limitation in the figures of the accompanying drawings. It should be noted that references to "an" or "one" embodiment in this disclosure are not necessarily to the same embodiment, and they mean at least one. In the drawings:

FIG. 3 illustrates an example set of operations for training a machine learning model to identify a wakefulness state of a user based on current user wakefulness data according to one or more embodiments;

DETAILED DESCRIPTION

In the following description, for the purposes of explanation, numerous specific details are set forth in order to provide a thorough understanding. One or more embodiments may be practiced without these specific details. Features described in one embodiment may be combined with features described in a different embodiment. In some examples, well-known structures and devices are described with reference to a block diagram form in order to avoid unnecessarily obscuring the present invention.

1. GENERAL OVERVIEW
2. SYSTEM ARCHITECTURE
3. CONFIGURING APPLICATIONS BASED ON DETECTED CURRENT USER WAKEFULNESS STATE
3.1 APPLYING SETS OF RULES TO CURRENT WAKEFULNESS DATA TO DETERMINE USER WAKEFULNESS STATE
3.2 DETERMINING USER WAKEFULNESS STATE BASED ON ENVIRONMENTAL WAKEFULNESS DATA
3.3 DETERMINING LEVELS OF USER WAKEFULNESS BASED ON CURRENT WAKEFULNESS DATA
4. TRAINING MACHINE LEARNING MODEL
5. EXAMPLE EMBODIMENT: CONFIGURING APPLICATION SETTINGS OF A DEVICE BASED ON DETECTING CURRENT WAKEFULNESS DATA
6. EXAMPLE EMBODIMENT: CLOUD-BASED WAKEFULNESS CONFIGURATION INTERFACE
7. COMPUTER NETWORKS AND CLOUD NETWORKS
8. MISCELLANEOUS; EXTENSIONS
9. HARDWARE OVERVIEW

1. General Overview

One or more embodiments train and apply a machine learning model to wakefulness data to compute a wakefulness state of a user. Wakefulness data includes any data that may be used to compute a wakefulness state of a user. Wakefulness data includes user data detected by a wearable device or sensor. Wakefulness data includes environmental data corresponding to an environment that includes a target user. Alternatively, or additionally, the system may apply a set of static rules to wakefulness data to compute the wakefulness state of a user.

The system configures applications and/or devices based on the computed wakefulness state of a user. In an example, a system may reduce or altogether stop visual, audible, or tactile notifications in response to determining that a user is asleep. The system may configure applications and/or devices to take actions based on a wakefulness state at a point-in-time and/or for a period of time. In an example, the system may turn off the television or lock the doors of a home in response to determining that a user has been asleep for thirty minutes.

One or more embodiments described in this Specification and/or recited in the claims may not be included in this General Overview section.

2. System Architecture

Figure 1:
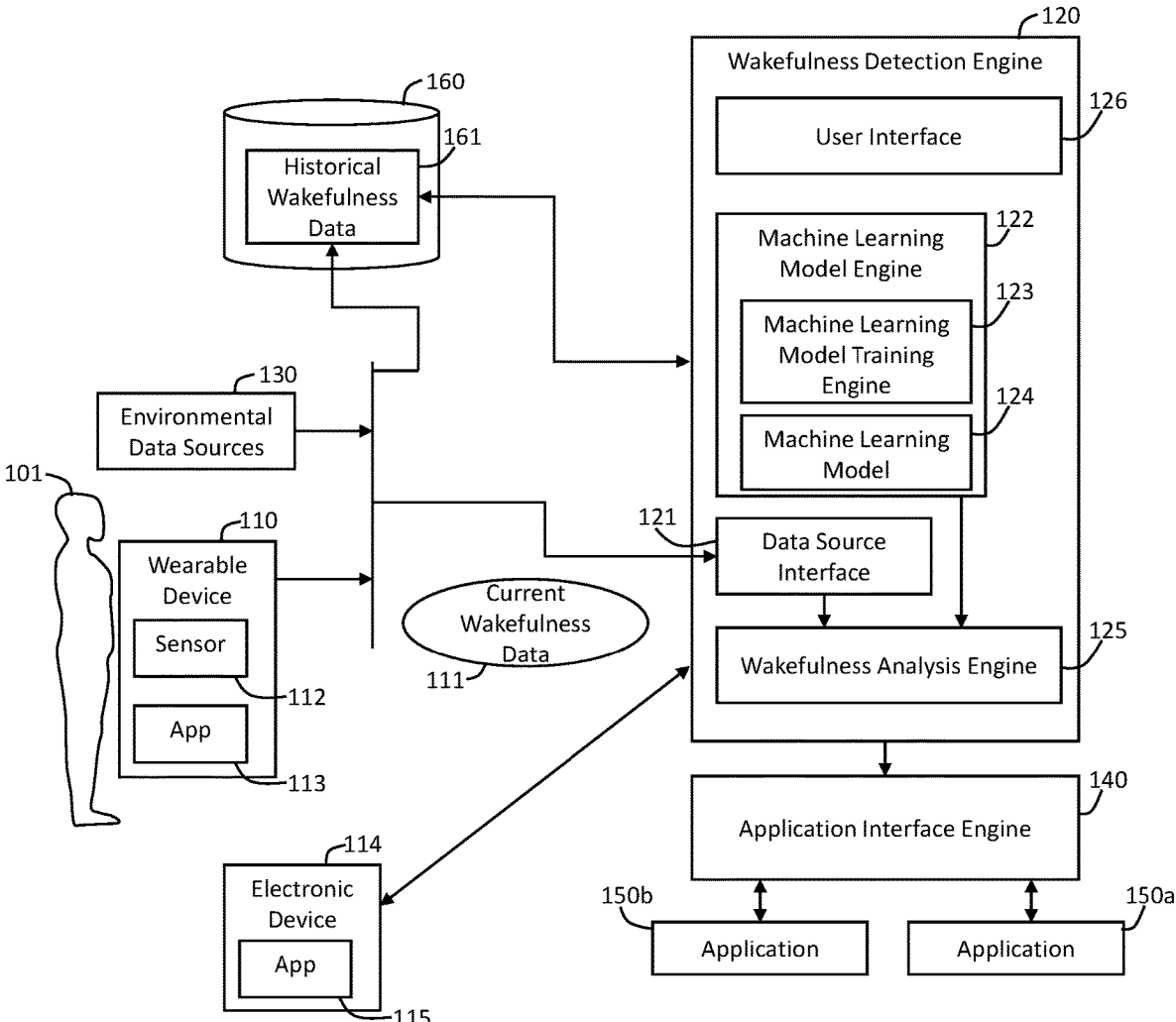
FIG. 1 illustrates a system in accordance with one or more embodiments.

FIG. 1 illustrates a system 100 in accordance with one or more embodiments. As illustrated in FIG. 1, system 100 includes a wearable device 110 and a wakefulness detection engine 120. The system 100 may further include environmental data sources 130, such as environmental sensors. The system 100 may further include one or more additional electronic devices 114 running one or more applications 115. For example, in one embodiment, the wearable device 110 is a watch and the electronic device 114 is a smart phone in wireless communication with the watch. The system includes an application interface engine 140 that interfaces with the wakefulness detection engine 120 to control one or more applications 150. A data repository 160 stores historical wakefulness data 161.

The wearable device 110 includes any type of device wearable by a user and capable of detecting characteristics of the user. Examples of wearable devices 110 include watches, bracelets, rings, headbands, and clothing. The wearable device 110 includes at least one sensor 112 that detects a characteristic of a user 101. In one or more embodiments, the wearable device 110 detects the characteristic to generate current wakefulness data 111 while the user wears the device 110. Examples of sensors 112 and characteristics include: a temperature sensor to measure a user's temperature, an optical sensor, pressure sensor, or accelerometer to measure a user's pulse, an accelerometer to measure body movement of the user, a microphone to measure noises made by the user, and a gyroscopic sensor to measure a body position of the user.

The wearable device 110 includes one or more applications 113. The applications 113 are programs that run on the wearable device 110 to perform functions using the components of the wearable device 110. Examples of applications include: alarms, media players, fitness trackers, financial services applications, messaging applications, email applications, and gaming applications. Embodiments are not limited by a class of application. Instead, one or more embodiments control functions of the applications 113 based on a detected wakefulness state of the user 101.

The system includes environmental data sources 130 that generate wakefulness data associated with the user 101. For example, a light sensor may detect a level of light in a room in which the user is located. A sound sensor may detect a sound level in an environment in which the user is located. Power sensors may detect whether devices, such as televisions, are on or off.

The data obtained from one or both of the sensors 112 of the wearable device 110 and the environmental data sources 130 constitute wakefulness data. The wakefulness detection engine 120 obtains the wakefulness data to determine a wakefulness state of the user 101. According to one example, the wakefulness data is provided to a data repository 160 to be stored as historical wakefulness data 161. In addition, or in the alternative, the wakefulness data may be transmitted to a wearable device interface 121 of the wakefulness detection engine 120 as current wakefulness data 111.

In one or more embodiments, a data repository 160 is any type of storage unit and/or device (e.g., a file system, database, collection of tables, or any other storage mechanism) for storing data. Further, a data repository 160 may include multiple different storage units and/or devices. The multiple different storage units and/or devices may or may not be of the same type or located at the same physical site. Further, a data repository 160 may be implemented or may execute on the same computing system as the wakefulness detection engine 120 or the wearable device 110. Alternatively, or additionally, a data repository 160 may be implemented or executed on a computing system separate from the wakefulness detection engine 120 or the wearable device 110. A data repository 160 may be communicatively coupled to the wearable device 110 and the wakefulness detection engine 120 via a direct connection or via a network.

Information describing historical wakefulness data 161 may be implemented across any of components within the system 100. However, this information is illustrated within the data repository 160 for purposes of clarity and explanation.

The wakefulness detection engine 120 analyzes the current wakefulness data 111 to determine whether the user 101 is currently awake or asleep. The wakefulness detection engine 120 interfaces with the application interface engine 140 to control functions of one or more applications 150*a*, 150*b*, or 113 based on the determination whether the user 101 is awake or asleep.

The wakefulness detection engine 120 includes a data source interface 121. The data source interface 121 obtains current sensor data from one or both of the wearable device 110 and the environmental data sources 130. The data source interface 121 may include processing elements such as signal processing circuitry, communications security program code executed by a processor, and transmission elements, such as an antenna or communications port. According to one example, the data source interface 121 includes a short-range wireless communication antenna and processing circuitry for receiving the current wakefulness data 111 wirelessly from one or both of the wearable device 110 and the environmental data sources 130. According to another example, the data source interface 121 includes a physical connector that physically engages with a communications port of the wearable device 110 to obtain the current wakefulness data 111.

In one embodiment, the wakefulness detection engine 120 includes a machine learning model engine 122 to train a machine learning model 124 based on historical wakefulness data 161 to determine whether the user 101 is awake or asleep. The machine learning model engine 122 includes a machine learning model training engine 123 to train a machine learning model 124 to determine whether the user 101 is currently awake or asleep. In one embodiment, the wakefulness detection engine 120 prompts a user via the user interface 126, or via the wearable device 110, to indicate whether the user 101 is awake or asleep. If the user replies, indicating the user is awake, the wakefulness detection engine 120 applies a corresponding "awake" label to a current set of sensor data and stores the data as historical wakefulness data 161. If the user does not reply, indicating the user may be asleep, the wakefulness detection engine 120 applies a corresponding "asleep" label to a current set of sensor data and stores the data as historical wakefulness data 161. According to alternative embodiments, the wakefulness detection engine 120 may apply "awake" or "asleep" labels to sets of current wakefulness data 111 using default rules and without requesting user input. The wakefulness detection engine 120 may allow a user 101 to modify the applied labels at a later time. For example, the wakefulness detection engine 120 may apply a default "awake" label to sets of current wakefulness data 111 obtained during daylight hours. The wakefulness detection engine 120 may apply a default "asleep" label to sets of current wakefulness data 111 obtained during nighttime hours. The wakefulness detection engine 120 may apply the "awake" label to sets of current wakefulness data 111 including movement levels, sound levels, or light levels that exceed threshold levels. The wakefulness detection engine 120 may apply the "asleep" label to sets of current wakefulness data 111 including movement levels, sound levels, or light levels that fail to exceed threshold levels.

The wakefulness analysis engine 125 analyzes the current wakefulness data 111 to determine whether a user is awake or asleep. In one embodiment, the wakefulness analysis engine 125 applies a predefined set of rules to the current wakefulness data 111 to make the determination. In another embodiment, the wakefulness analysis engine 125 applies the machine learning model 124 to the current wakefulness data 111 to make the determination.

The wakefulness detection engine 120 may provide to the user a set of times for which "awake" and "asleep" labels were assigned via the user interface 126 or via the wearable device 110. The user may review the times and labels and may provide feedback to alter the labels. According to one embodiment, the wakefulness detection engine 120 uses the sets of wakefulness data and corresponding labels to generate a set of rules that specify when the wakefulness analysis engine 125 will determine that a user is "awake" or "asleep." For example, the set of rules may include rules such as the following: (1) a user is always awake if detected movement exceeds a threshold, (2) a user is always awake if detected pulse rate exceeds a threshold, (3) a user is awake if [time=daylight hours], unless: (a) pulse rate [is less than] [defined pulse rate], (4) a user is asleep if [time=nighttime], and (a) pulse rate [is less than] [defined pulse rate]. The set of rules may be prioritized such that if (1) is true, the wakefulness analysis engine 125 determines the user is awake, regardless of time of day and pulse rate. The foregoing examples of rules include only a few examples. Embodiments include rules associated with many different data sources, including light sensors, sound sensors, accelerometers, and devices in the user's environment.

According to an alternative embodiment, the machine learning model training engine 123 uses the sets of wakefulness data and corresponding labels to train the machine learning model 124 to assign a wakefulness state, such as "awake" or "asleep" to a user. In such an embodiment, the machine learning model training engine 123 may assign initial wakefulness labels to sets of historical wakefulness data. The machine learning model training engine 123 may obtain user input indicating whether the initial wakefulness labels are accurate. The machine learning model training engine 123 updates the trained machine learning model 124 based on the user input In addition to the binary wakefulness states, "awake" and "asleep," the wakefulness analysis engine 125 may assign sub-states of sleep to the user 101, such as stages 1-4, random eye movement (REM), and deep sleep. The wakefulness analysis engine 125 may assign sub-states of wakefulness to the user 101, such as "vigorous activity," "light activity," "sedentary," "resting," "preparing for sleep," and "waking up."

The wakefulness detection engine 120 interfaces with an application interface engine 140 to control the functionality of one or more applications 150a, 150b, 113, and 115. The applications 150a and 150b are third-party applications that communicate with one or both of the wearable device 110 and the additional electronic device 114. For example, a user may interface with a website of a financial institution to receive notifications from the financial institution on their wearable device 110 or on the electronic device 114. In this example, the application 150a may be a notification application maintained by the financial institution for sending notifications. In one embodiment, the application interface engine 140 is a cloud-based engine having functionality for setting and modifying communications settings for applications 150a and 150b that communicate with the wearable device 110. In addition, or in the alternative, the application interface engine 140 may interact directly with the wearable device 110 to control functions, such as sounds, vibrations, and displays, performed by the wearable device 110 or the additional electronic device 114. According to yet another example, the application interface engine 140 provides a cloud-based interface for users to set notifications settings of applications 113 executed on the wearable device 110 or the electronic device 114. For example, the application interface engine 140 may display via the user interface 126 a list of applications 113 or 115 executing on the wearable device 110 or electronic device 114 and functions that may be performed by the applications 113 or 115. A user may select, for individual applications or for sets of two or more applications, what types of functions may be performed based on a determination that the user is awake or asleep. For example, the user may select, for every application 113 a setting that no vibration alerts and no visual alerts may be generated when the user is asleep. The user may further select a setting to allow audio alerts from an alarm application, but not from other applications, when the user is sleeping. The application interface engine 140 may update the settings of the applications 113 and 115 in the wearable device 110 and the additional electronic device 114 based on the user selections via the user interface 126.

In one or more embodiments, interface 126 refers to hardware and/or software configured to facilitate communications between a user and one or both of the wakefulness detection engine 120 and the application interface engine 140. Interface 126 renders user interface elements and receives input via user interface elements. Examples of interfaces include a graphical user interface (GUI), a command line interface (CLI), a haptic interface, and a voice command interface. Examples of user interface elements include checkboxes, radio buttons, dropdown lists, list boxes, buttons, toggles, text fields, date and time selectors, command lines, sliders, pages, and forms.

In an embodiment, different components of interface 126 are specified in different languages. The behavior of user interface elements is specified in a dynamic programming language, such as JavaScript. The content of user interface elements is specified in a markup language, such as hypertext markup language (HTML) or XML User Interface Language (XUL). The layout of user interface elements is specified in a style sheet language, such as Cascading Style Sheets (CSS). Alternatively, interface 126 is specified in one or more other languages, such as Java, C, or C++.

In one or more embodiments, the system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

Additional embodiments and/or examples relating to computer networks are described below in Section 7, titled "Computer Networks and Cloud Networks."

In one or more embodiments, the wakefulness detection engine 120 refers to hardware and/or software configured to perform operations described herein for determining the wakefulness of the user 101. Examples of operations for determining the wakefulness of the user 101 are described below with reference to FIG. 2.

In an embodiment, the wakefulness detection engine 120 is implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/ or transmitter, a base station, a communication management device, a router, a switch, a controller, an access point, and/or a client device.

In one or more embodiments, a tenant (such as tenant 112 and/or tenant 114) is a corporation, organization, enterprise or other entity that accesses a shared computing resource, such as application 116. In an embodiment, tenant 112 and tenant 114 are independent from each other. A business or operation of tenant 112 is separate from a business or operation of tenant 114.

3. Configuring Applications Based on Detected Current User Wakefulness State

Figure 2:
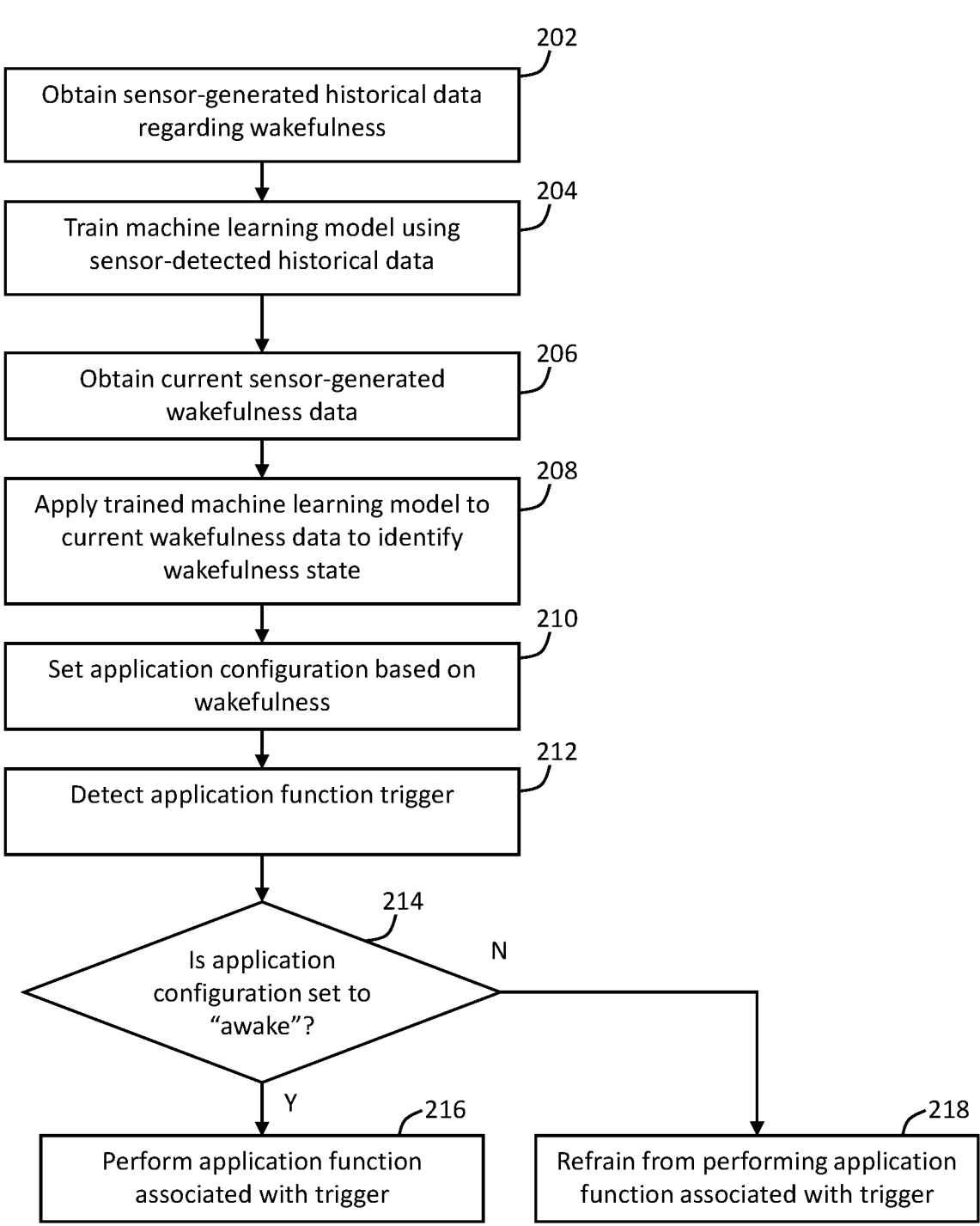
FIG. 2 illustrates an example set of operations for configuring applications based on a current user wakefulness state in accordance with one or more embodiments.

FIG. 2 illustrates an example set of operations for controlling functions of applications associated with a wearable device based on in accordance with one or more embodiments. One or more operations illustrated in FIG. 2 may be modified, rearranged, or omitted all together. Accordingly, the particular sequence of operations illustrated in FIG. 2 should not be construed as limiting the scope of one or more embodiments.

A system obtains sensor-generated historical data associated with a user's wakefulness (Operation 202). The sensor-generated historical data includes sensor data from one or more sensors of a wearable device. In addition, or in the alternative, the sensor data may be from one or more environmental sensors in an environment in which a user sleeps. In addition to sensor data, the system may obtain operational data from the wearable device or one or more devices in a designated environment. The operational data may indicate an operational state of the one or more devices. For example, the system may obtain information regarding whether a television is on or off, whether a user is actively engaging with a computer-based application, or whether lights are on or off in a sleeping environment. Examples of sensor-generated data from the wearable device include: breathing rate, heart rate, movement levels of the wearable device, body temperature, and detected sounds. Examples of operational data generated by the wearable device include: time of day, data indicating a user is actively interacting with an application on the device, and data indicating the device is generating light or sounds. Examples of environmental sensor data include: sounds in an environment, light levels in an environment, a temperature in an environment, and movement levels in an environment. Examples of operational data associated with devices in an environment include: data indicating that a device is on or off, data indicating a device is generating light or sounds, and data indicating a user is interacting with a device in an environment. In addition, in one or more embodiments the system obtains data associated with historical wakefulness patterns of a user. For example, a user may designate a sleeping pattern in which the user is active at night and sleeps during the day.

The system trains a machine learning model using the sensor-detected historical data to identify a wakefulness of a user (Operation 204). In one embodiment, the machine learning model is a neural net trained with sets of sensor data and associated wakefulness labels. For example, one set of sensor data associated with one period of time may be assigned a label, "awake." Another set of sensor data associated with another period of time may be assigned with a label, "asleep." In one embodiment, the system associates the labels with the sets of sensor data based on user input. For example, they system may, prompts a user to assign labels to multiple different sets of data corresponding to multiple different time periods. According to another example, the system may generate user prompts on a wearable device at different points of time and in different situations. The system may determine that if the user responded to the prompt, the user was awake. The system may assign the label, "awake," to a corresponding data set. If the user does not respond, the system may assign a label, "asleep," to the corresponding data set.

According to yet another embodiment, the system may apply "awake" or "asleep" labels to sets of sensor data associated with different periods of time using default rules and without requesting user input. For example, the system may assign a default "asleep" label to sets of data obtained from 10 PM to 6 AM in which a level of sensed movement is less than a threshold level. The system may generate a graphical user interface (GUI) to allow the user to change one or more labels for one or more associated sets of sensor data prior to training the machine learning model.

Upon training the machine learning model, the system obtains a set of current sensor-generated wakefulness data (Operation 206). For example, the user may wear a device, such as a watch, a wristband, or a ring that generates sensor data and transmits the sensor data to the system at regular intervals. In addition, or in the alternative, one or more environmental sensors or data-generating devices may provide wakefulness data to the system. For example, the system may obtain noise data regarding an environment in which the user designates as a sleeping environment. Alternatively, or in addition, the system may obtain operational data of one or more devices in the environment, such as data indicating that a television is on, that lights are on, or that movement exceeding a threshold is detected in the environment.

The system applies the trained machine learning model to the current wakefulness data to identify a wakefulness state of a user (Operation 208). The machine learning model may be trained to identify a wakefulness state based on one or both of (a) sensor or operational data generated by a wearable device, and (b) sensor or operational data of one or more devices in an environment designated as a sleeping environment by the user. For example, a machine learning model may identify a wakefulness state of a user based on: (a) environmental data identifying a time of day, (b) environmental data indicating the television is turned on, (c) sensor data from the wearable device indicating a pulse rate of the user, (d) sensor data from the wearable device indicating a level of movement of the wearable device, (e) environmental sensor data indicating a noise level in an environment in which the user is located, (f) operational data from the wearable device indicating whether the user is actively interacting with an application of the wearable device, and (g) a user-defined historical sleep cycle for the user.

The system sets a configuration setting of one or more applications on one or more devices based on the identified wakefulness state of the user (Operation 210). The one or more devices may include the wearable device, or another device associated with the user. For example, in an embodiment in which the wearable device is a wristband and a phone is wirelessly paired with the wristband, the system may configure settings of the phone based on the data generated by the wristband. According to one embodiment, the system communicates with a notification settings application of a device to globally configure the settings for all the application running on the device. For example, the system may place the phone in an "awake" configuration or an "asleep" configuration. In an "awake" configuration, a predefined set of applications running on the device may be permitted to generate audio, visual, and tactile notifications. In an "asleep" configuration, a predefined set of applications running on the device may be prevented from generating audio, visual, or tactile notifications.

According to an alternative embodiment, the system may configure settings for individual applications on a device. For example, when a phone is configured in an "asleep" wakefulness setting, one set of applications may be permitted to generate sound notifications, another set of applications may be permitted to generate tactile notifications, and a third set of applications may be prevented from generating any audio, visual, or tactile notifications. In addition, the system may configure settings for different functions of different applications. For example, the system may configure a voice calling application to permit the voice calling application to generate an audio notification when a call is received from one phone number and to refrain from generating the audio notification when a call is received from any other phone number.

According to one embodiment, the system may communicate with a cloud-based application that controls settings of applications on a device. For example, one application may control the functionality of a television. The application may include an Internet-based webpage that interfaces with a client on the television to control functionality of the television. Another application may control lights in an environment. The application may include an Internet-based web-page that communicates with a local wireless network in an environment in which the lights are located to control the functionality of the lights. Another application may send text messages to a phone. The application may include an Internet-based webpage that tracks information associated with the user and sends messages to a phone number based on detecting particular content in the tracked information. For example, a banking application may track a user's account balance and generate a text message based on detecting the account balance corresponding to a predefined threshold.

In one or more embodiments, the system may provide a user with a GUI to set configuration settings for individual applications on the same device based on a user's wakefulness. For example, a user may select a voice calling application and indicate that the voice calling application may generate an audible sound and vibration on a phone when a call is received from a particular phone number when the system detects the user is "asleep." The user may further configure the voice call application settings to prevent the voice call application from generating audible or tactile notifications when a voice call is received from any other phone numbers when the system detects the user is "asleep." The user may further configure wakefulness settings for one or more social media applications to prevent the social media applications from generating audible or tactile outputs from a wearable device when the system detects the user is "asleep." The user may configure wakefulness settings of a television to control the television to turn off when the system detects the user is "asleep."

The system detects an application function trigger (Operation 212). For example, a text messaging application on a phone may have a notification functionality of vibrating the phone and making an audible sound when a message is received by the phone. A voice calling application of a phone may have functionality of emitting a ringing sound when a call is received. An alarm function of a wristband wearable device may have a functionality of emitting a sound and flashing a light when a designated time is detected. A television may execute applications having the functionality of displaying video and emitting audio when a user selects a particular program to watch. Social media applications on a wearable device may have the functionality of generating an audible sound when a new social media post is detected.

The system determines whether the application configuration for the particular application is set to "awake," indicating that the system detected the user was awake (Operation 214). For example, if the detected trigger is an incoming telephone call, the system determines whether a configuration setting for the voice calling application of a phone is set to "awake" or "asleep" based on the current wakefulness data. According to another example, if the detected trigger is a predetermined period of time passing while a television is on, the system determines whether the configuration setting for the video application of the television is set to "awake" or "asleep." In one example in which the application is a global notification settings application for a phone, the incoming trigger may be any communication that would trigger an audio, visual, or tactile output from the phone.

If the configuration settings for the application are set to an "awake" wakefulness setting, the system allows the application to perform the function associated with the application function trigger (Operation 216). In the example in which the application function trigger is an incoming telephone call, the system allows the voice calling application of the phone to generate an audible and tactile notification that a call has been received. In the example in which the application function trigger is a predetermined period of time passing while a television is on, the system allows the video application of the television to display video and emit audio. In another example in which the application function trigger is a notification that a post has been detected on a social media application on a wearable device, the system allows the social media application to control the wearable device to emit a notification sound.

If the configuration settings for the application are not set to "awake" (such as if the settings are set to "asleep"), the system prevents the application from performing the function associated with the application function trigger (Operation 218). In the example in which the application function trigger is an incoming telephone call, the system prevents the voice calling application of the phone from generating an audible and tactile notification that a call has been received. In the example in which the application function trigger is a predetermined period of time passing while a television is on, the system controls the television to stop the video application and turn off the television. In the example in which the application function trigger is a notification that a post has been detected on a social media application on a wearable device, the system prevents the social media application from generating a notification sound via the wearable device.

According to the embodiment described above, the system detects a wakefulness state of a user based on currently-obtained sensor and/or operational data of a wearable device and/or environmental devices and controls the functionality of one or more applications or devices based on the currently-detected wakefulness state.

3.1. Applying Static Sets of Rules to Current Wakefulness Data to Determine User Wakefulness State In one or more embodiments, the system applies a set of static rules to current wakefulness data to identify a wakefulness state of a user, without applying a machine learning model to the current wakefulness data.

For example, a wearable device may include one or more sensors to generate current wakefulness sensor data including (a) movement sensor data, (b) pulse rate sensor data, and (c) user body temperature sensor data. The system may obtain the current wakefulness sensor data and apply a static set of rules, including:

(1) Set user wakefulness to "awake" if a movement level exceeds a threshold movement level for a predetermined period of time.

(2) Set user wakefulness to "awake" if pulse rate exceeds a threshold pulse rate for a predetermined period of time.

(3) Set user wakefulness to "asleep" if a current time is between 10 PM and 6 AM, unless rule (1) or rule (2) applies.

(4) Set user wakefulness to "asleep" if pulse rate is less than a threshold pulse rate, and user body temperature is within a threshold range, unless rule (1) applies.

(5) Set user wakefulness to "awake" if a current time is between 6 AM and 10 PM, unless rule (4) applies.

The system may obtain the current wakefulness data and apply the predefined set of rules to the wakefulness data to identify the wakefulness state of a user. In one or more embodiments, the system generates a GUI to allow a user to create, delete, and modify the set of rules.

3.2. Determining User Wakefulness State Based on Environmental Wakefulness Data

In one or more embodiments, the system determines a user's wakefulness state based on environmental sensor data and operational data of one or more devices in the environment. For example, the system may determine the user's wakefulness state based on the environmental sensor data and operational data without using sensor data from a wearable device. Examples of environmental sensor data include: sounds in an environment, light levels in an environment, a temperature in an environment, and movement levels in an environment. Examples of operational data associated with devices in an environment include: data indicating that a device is on or off, data indicating a device is generating light or sounds, and data indicating a user is interacting with a device in an environment.

The system may identify a particular environment in which one or more devices are located for determining the user's wakefulness state. For example, the system may identify a television, a computer, a motion sensor, and a temperature sensor in a bedroom. In one embodiment, the system may analyze network connection data to determine whether a portable computing device, such as a laptop or phone, is located in the particular environment. For example, if a home includes a physical network port in a particular environment, the system may determine that a portable device is in the particular environment. The system may obtain sensor or operational data from the portable device when it is located in the particular environment. The system may refrain from obtaining the sensor or operational data from the particular device when it is not located in the particular environment.

According to an example, embodiment, the system obtains sensor and operational data from one or more devices in the particular environment to identify a light level and sound level in the particular environment at a particular time. The system may apply a machine learning model or a set of rules to the environmental sensor data and operational data for one or more devices in the particular environment to identify the wakefulness state of a user. The system controls configuration information of one or more applications associated with one or more devices based on the determined wakefulness state of the user.

3.3. Determining Degrees of User Wakefulness Based on Current Wakefulness Data

In one or more embodiments, the system identifies degrees of user wakefulness. For example, a machine learning model, or a static set of rules, may be applied to current wakefulness data to identify a user as having a 20%, 60%, or 75% degree of wakefulness. A system may configure applications and devices according to the degree of wakefulness of the user. For example, the system may configure a voice calling application to generate audible notifications corresponding to incoming calls from unknown phone numbers based on a user having a degree of wakefulness of 90% or higher. If the machine learning model determines the user has a degree of wakefulness less than 90%, the system may configure the voice calling application to refrain from generating audible notifications upon receiving incoming calls from unknown callers. The system may additionally allow the voice calling application to generate audible and tactile notifications corresponding to messages from contacts identified as "friends" based on determining the degree of wakefulness of the user is 70% or higher. The system may additionally allow the voice calling application to generate audible, tactile, and visual notifications corresponding to messages from a contact identified as a "spouse" based on determining the degree of user wakefulness is 40% or higher. The system may allow a user to configure applications based on the degree of wakefulness.

In one or more embodiments, the system may identify one or more sleep stages associated with a degree of wakefulness of the user. The system may identify the degree of wakefulness of the user and sleep stages associated with the degrees of wakefulness based on sensor data generated by a wearable device. The system may obtain sensor data associated with (a) user body movements, (b) user heartbeat, (c) user blood pressure, and (d) user breathing to determine a sleep stage of a user.

For example, the system may detect a slowing heartbeat and breathing and occasional body movements to identify a user as being in non-rapid eye movement (NREM) stage 1 associated with a 40% degree of wakefulness. The system may detect a lowering body temperature and even breathing and heart rate to identify a user as being in NREM stage 2 associated with a 10% degree of wakefulness. The system may detect minimal body movement, reduced blood pressure, and slower breathing to identify the user as being in NREM stage 3, associated with a 0% degree of wakefulness. The system may detect minimal body movement and faster and irregular breathing to identify the user as being in a rapid-eye movement (REM) stage of sleep, associated with a 0% degree of wakefulness.

4. Training Machine Learning Model

FIG. 3 illustrates an example set of operations for training a machine learning model to identify a wakefulness state of a user, in accordance with one or more embodiments. One or more operations illustrated in FIG. 3 may be modified, rearranged, or omitted all together. Accordingly, the particular sequence of operations illustrated in FIG. 3 should not be construed as limiting the scope of one or more embodiments.

FIG. 3 illustrates an example of a set of operations for training a machine learning model, such as a neural network or support vector machine (SVM), that use a stochastic optimization of the weights, according to one or more embodiments.

A system obtains a set of historical data including historical sensor data of a wearable device, historical sensor data from one or more devices in a particular environment, and historical operational data of one or more devices associated with a user (Operation 302). The historical data may also include identified wakefulness labels associated with sets of sensor values and device operational data. In one embodiment, the system applies predefined rules to the historical sensor data and device operational data to label the sets of data as corresponding to an "awake" or "asleep" wakefulness state. In addition, or in the alternative, the system may allow a user to assign or modify labels associated with sets of sensor data and device operational data.

The system generates a training data set from the set of historical data (Operation 304). The training data set includes sensor values and wakefulness values associated with the set of sensor values. For example, one data point in the set of training data includes a set of sensor data values for a wearable device associated with a predetermined period of time and a label associating the set of training data with an "awake" state of a user. Another data point in the set of training data includes another set of sensor data values and another label associating the set of training data with an "asleep" state of the user.

The system applies a machine learning algorithm to the training data set to train the machine learning model to assign labels identifying wakefulness states to different sets of sensor values (Operation 406). For example, the system may identify a particular combination of body temperature sensor data, noise sensor data, motion sensor data, and heart rate sensor data as being associated with an "awake" wakefulness state of the user. The system may identify another combination of body temperature sensor data, noise sensor data, motion sensor data, and heart rate sensor data as being associated with an "asleep" wakefulness state of the user.

In one embodiment, training the machine learning model includes receiving feedback for the wakefulness state identified by the machine learning model for sets of sensor values (Operation 308). For example, the system may display a list of data points and times at which the data points were obtained. The system may further display sensor data associated with a data point. The system displays the wakefulness state assigned to the data point by the machine learning model. A user may modify the assigned wakefulness state. For example, if a user determines that for a particular data point, the machine learning model incorrectly assigned an "asleep" label to the data point when the user was merely resting, the user may change the label associated with the data point to "awake."

The system updates the machine learning model based on the feedback (Operation 310). For example, the system may modify coefficients assigned to nodes of a neural network to generate, for the particular data point for which the user modified the wakefulness label, the same label that was selected by the user.

5. Example Embodiment: Configuring Application Settings of a Device Based on Detecting Current Wakefulness Data Detailed examples are described below for purposes of clarity. Components and/or operations described below should be understood as one specific example which may not be applicable to certain embodiments. Accordingly, components and/or operations described below should not be construed as limiting the scope of any of the claims.

Figure 4:
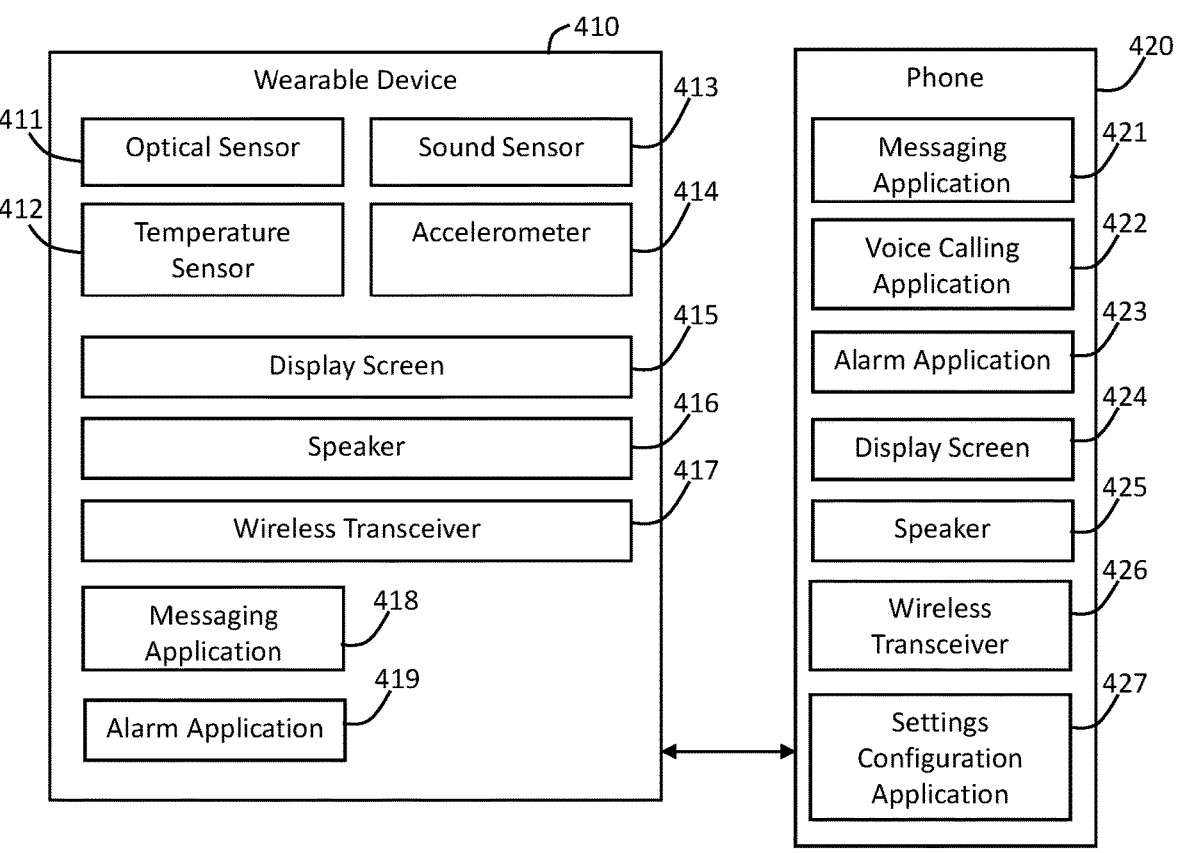
FIG. 4 illustrates an example embodiment of a system for configuring applications based on a current wakefulness state of a user.

FIG. 4 illustrates an example embodiment of a system for configuring application settings of one or more devices. The system includes a wearable device 410 and a phone 420. When worn by a user, the wearable device 410 generates sensor data corresponding to characteristics of the user. A settings configuration application 427 of the phone 420 analyzes the sensor data to determine a wakefulness state of the user and to configure application settings for one or both of the wearable device 410 and the phone 420.

The wearable device 410 includes an optical sensor 411 to measure one or both of a blood pressure and a pulse rate of the user. A temperature sensor 412 measures a skin temperature of the user. A sound sensor 413, such as a microphone, measures sounds made by the user. An accelerometer 414 measures movements of the user. In an example in which the wearable device is a watch or wristband, the accelerometer 414 measures movement of the wrist on which the watch or wristband is fastened.

The wearable device 410 also includes a display screen 415 to display images and data visually and a speaker 416 to generate sounds. A wireless transceiver 417 includes an antenna to communicate with a wireless transceiver 426 of the phone 420.

The wearable device includes a messaging application 418 and an alarm application 419. The messaging application 418 interfaces with the display screen 415 to generate a visual notification of a received message and to display content of messages. The messaging application 418 interfaces with the speaker 416 to emit a sound notifying a user of a received message. The alarm application 419 interfaces with the display screen 415 to generate a visual display when an alarm time is detected by the alarm application 419. The alarm application 419 also interfaces with the speaker 416 to generate a sound when an alarm is triggered.

The phone 420 includes applications that interface with devices on the phone to perform operations associated with the devices. Applications include a messaging application 421 for sending and receiving text messages. The messaging application 421 interfaces with the display screen 424 to generate a visual notification of a received message and to display content of messages. The messaging application 421 interfaces with the speaker 425 to emit a sound notifying a user of a received message. A voice calling application 422 sends and receives voice calls. The voice calling application 422 interfaces with the display screen 424 to generate a visual notification of an incoming call. The voice calling application 422 interfaces with the speaker 425 to emit a sound notifying a user of an incoming call. An alarm application 423 interfaces with the display screen 424 to generate a visual display when an alarm time is detected by the alarm application 423. The alarm application 423 also interfaces with the speaker 425 to generate a sound when an alarm is triggered.

The wireless transceiver 426 may include a cellular antenna for sending and receiving data via a cellular network. The wireless transceiver 426 may also include a near field antenna for communicating with the wireless transceiver 417 of the wearable device 410. The wireless transceiver 426 may also include a Wi-Fi antenna for communicating with a local area network.

The settings configuration application 427 obtains current wakefulness data from the wearable device 410. In the example embodiment of FIG. 4, the current wakefulness data includes current sensor data from the optical sensor 411, the temperature sensor 412, the sound sensor 413, and the accelerometer 414. The settings configuration application 427 analyzes the current wakefulness data to determine whether a user is awake or asleep. In one embodiment, the settings configuration application applies a trained machine learning model to the current wakefulness data to determine whether the user is awake or asleep. In an alternative embodiment, the settings configuration application applies a set of rules to the current wakefulness data to determine whether the user is awake or asleep.

The settings configuration application 427 modifies the settings of one or more of the messaging application 418, the alarm application 419, the messaging application 421, the voice calling application 422, and the alarm application 423 based on the determination of the wakefulness of the user. For example, the settings configuration application 427 may disable one or more alarms of the alarm application 419 or the alarm application 423 responsive to determining a user is awake. In one embodiment, the settings configuration application 427 changes an alarm setting in the alarm applications 419 and 423 to turn off the alarms. In another embodiment, the settings configuration application 427 changes settings associated with the display screens 415 or 424 or the speakers 416 or 425 to prevent the alarm applications 419 and 423 from generating visual or audio notifications. The settings configuration application 427 may enable the alarms based on determining the user is asleep.

In addition, the settings configuration application 427 may configure settings of one or both of the messaging application 418 and the messaging application 421 to prevent the applications 418 and 421 from generating visual or audio notifications based on determining the user is asleep. In one embodiment, the settings configuration application 427 changes settings in the applications 418 and 421 to turn off notifications. In another embodiment, the settings configuration application 427 changes settings associated with the display screens 415 or 424 or the speakers 416 or 425 to prevent the messaging applications 418 and 421 from generating visual or audio notifications. The settings configuration application 427 may enable the notifications based on determining the user is awake.

Figure 5:
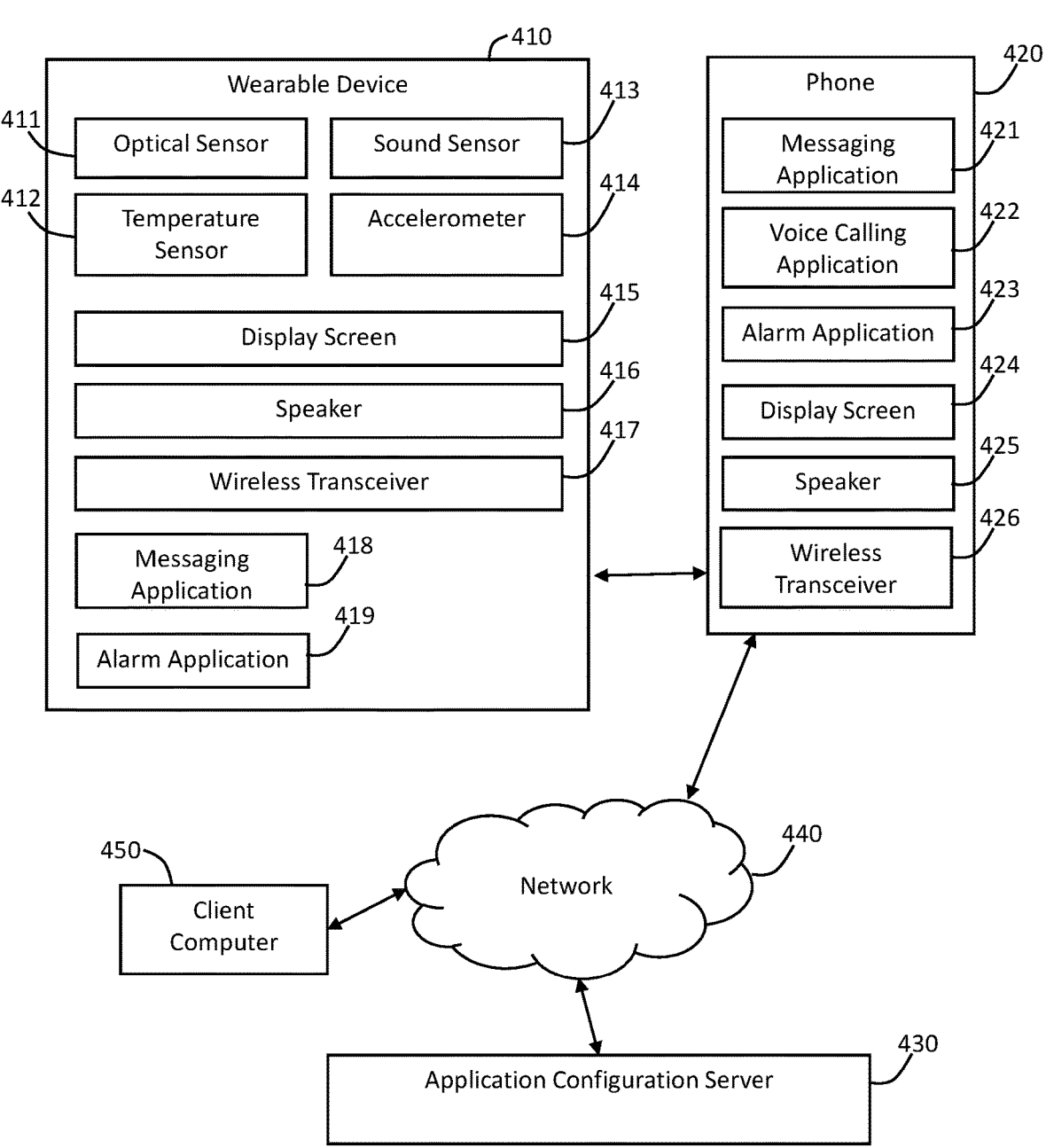
FIG. 5 illustrates another example embodiment of a system for configuring applications based on a current wakefulness state of a user.

Referring to FIG. 5, the application settings may be configured by a remote application configuration server 430 instead of an application in the phone 420. The wearable device 410 may be configured to transmit the current wakefulness data to the application configuration server 430 via the phone 420 and a network 440. The network 440 may include multiple networks, such as a cellular network, a local area network, and a wide area network, such as the Internet. The wearable device 410 may transmit the current wakefulness data to the network 440 via the phone 420 or directly via the wireless transceiver 417.

The application configuration server 430 receives the current wakefulness data and analyzes the current wakefulness data to determine whether a user is awake or asleep. In one embodiment, the settings configuration application applies a trained machine learning model to the current wakefulness data to determine whether the user is awake or asleep. In an alternative embodiment, the settings configuration application applies a set of rules to the current wakefulness data to determine whether the user is awake or asleep.

The settings configuration application 427 modifies the settings of one or more of the messaging application 418, the alarm application 419, the messaging application 421, the voice calling application 422, and the alarm application 423 based on the determination of the wakefulness of the user.

In one embodiment, a user may modify wakefulness state settings of one or more of the messaging application 418, the alarm application 419, the messaging application 421, the voice calling application 422, and the alarm application 423 via a client computer 450 in communication with the network 440. The application configuration server 430 may provide data to the client computer 450 to display a GUI on the client computer 450 displaying the applications on the wearable device 410 and the phone 420 having configurations that are modifiable by the user. The user may interact with the GUI to modify wakefulness settings. For example, the user may modify a wakefulness setting of the voice calling application 422 to allow the voice calling application 422 to generate a notification sound via the speaker 425 when a call is received from a particular phone number while the voice calling application 422 is configured based on a user's "asleep" state. The user may modify the wakefulness settings of the voice calling application 422 to prevent the voice calling application 422 from generating notification sounds via the speaker 425 when calls are received from other phone numbers while the voice calling application 422 is configured based on a user's "asleep" state.

In operation, the application configuration server 430 receives the current wakefulness data and sets the wakefulness state configurations for the applications 418, 419, 421, 422, and 423. The conditions of the wakefulness state configurations may have been previously set by the user via the client computer 450. If a triggering event occurs, such as a message being received by the messaging application 418, the messaging application 418 determines whether an operation associated with the triggering event may be executed by the messaging application 418 based on whether the messaging application 418 is in a configuration associated with an "awake" state of a user or an "asleep" state of the user. If the messaging application 418 is in the configuration associated with the "awake" state, the messaging application 418 may generate a sound via the speaker 416 to notify a user of a received message. If the messaging application 418 is in the configuration associated with the "asleep" state, the messaging application 418 may refrain from generating a sound via the speaker 416 to notify a user of a received message.

6. Example Embodiment: Cloud-Based Wakefulness Configuration Application

Figure 6:
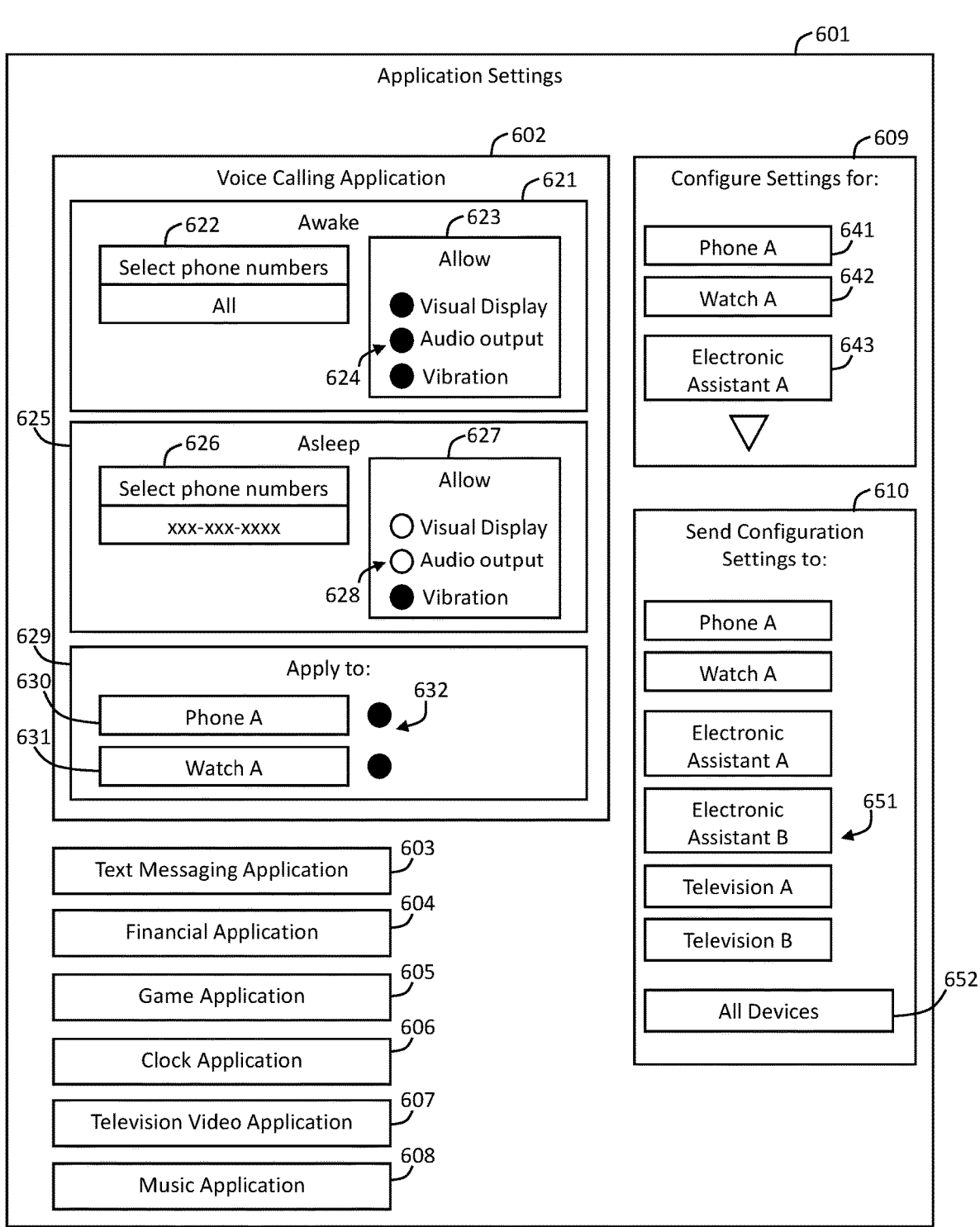
FIG. 6 illustrates an example embodiment of a graphical user interface for configuring devices and applications based on detected wakefulness settings.

FIG. 6 illustrates a graphical user interface (GUI) for a cloud-based wakefulness settings configuration application. The GUI includes an application settings screen 601 displaying data associated with devices and applications. The GUI allows the user to interact with interface elements to change application and device settings associated with detected wakefulness states of a user.

The application settings screen 601 includes selectable interface elements 602-608 for different applications executing on multiple different devices. In the example illustrated in FIG. 6, the interface elements include interface elements for applications include a voice calling application 602, a text messaging application 603, a financial application 604, a game application 605, a clock application 606, a television video application 607, and a music application 608.

The application setting screen 601 includes a device selection interface element 609 to allow a user to select particular devices for setting configuration settings. In the example illustrated in FIG. 6, the devices include a phone (Phone A) 641, a watch (Watch A) 642, and an electronic assistant (Electronic Assistant A) 643. The device selection interface element 609 may allow a user to select particular applications associated with the selected device. In addition, or in the alternative, the device selection interface element 609 may allow a user to set global wakefulness settings for all applications executing on the selected device. For example, selection of the icon Phone A 641 by a user may result in a display of each application executing on Phone A that may have wakefulness settings configured by a user. In addition, the GUI may display an interface element to set a global configuration for Phone A, such as an interface element to prevent any application executing on Phone A from emitting an audible sound when the detected wakefulness state of the user is "asleep."

Selection of a particular application interface element 602-608 results in the GUI displaying configuration settings for the associated application. In the example illustrated in FIG. 6, the voice calling application interface element 602 includes an "Awake" field 621 for setting configurations for the voice calling application when the wakefulness state of the user is "awake." The "Awake" field 621 includes a field 622 for selecting one or more phone numbers to which selected configuration settings will apply. The "Awake" field 621 further includes a field 623 including selectable radio elements 624 indicating the types of functions that may be initiated by the voice calling application when the wakefulness state of the user is "awake." In the example illustrated in FIG. 6, the voice calling application may generate a visual display, an audio output, and a vibration for all incoming phone numbers when a current user wakefulness state is "awake."

An "Asleep" field 625 includes a field 626 for selecting one or more phone numbers to which selected configuration settings will apply. The "Asleep" field 625 further includes a field 627 including selectable radio elements 628 indicating the types of functions that may be initiated by the voice calling application when the wakefulness state of the user is "asleep." In the example illustrated in FIG. 6, the voice calling application may generate a vibration for a specified phone number when a current user wakefulness state is "asleep."

A "device" field 629 lists devices 630 and 631 on which the voice calling application is installed. The "device" field 629 includes selectable radio icons 632 to allow a user to select on which device the selected configurations settings will be applied. In the example illustrated in FIG. 6, the settings are applied to a phone (Phone A) and a watch (Watch A).

Selection of any one of the selectable interface elements 603-608 results in the GUI displaying configuration settings for the associated device. For example, selecting the interface element 605 associated with a game applications results in the GUI displaying selectable interface elements to allow a user to configure visual, audible, and tactile settings for the game application on any devices on which the game application is installed and according to the detected current wakefulness state of a user.

The application settings screen 601 includes a field 610 for sending configuration settings selected by a user to the respective devices. In the example illustrated in FIG. 6, a user may send configuration settings to individual devices by selecting associated interface elements 651 or to all devices by selecting the interface element 652.

In one embodiment, a cloud-based application stores and manages the configuration settings information displayed by the application settings screen 601. The cloud-based application may communicate with devices associated with the user, including wearable devices, portable communications devices, and other devices in an environment specified by the user, via one or more networks connected to the cloud. For example, the cloud-based application may send configuration information to a phone via the Internet and a local area network. The phone may send particular configuration for a wearable device to the wearable device via near field communication.

7. Computer Networks and Cloud Networks

In one or more embodiments, a computer network provides connectivity among a set of nodes. The nodes may be local to and/or remote from each other. The nodes are connected by a set of links. Examples of links include a coaxial cable, an unshielded twisted cable, a copper cable, an optical fiber, and a virtual link.

A subset of nodes implements the computer network. Examples of such nodes include a switch, a router, a firewall, and a network address translator (NAT). Another subset of nodes uses the computer network. Such nodes (also referred to as "hosts") may execute a client process and/or a server process. A client process makes a request for a computing service (such as, execution of a particular application, and/or storage of a particular amount of data). A server process responds by executing the requested service and/or returning corresponding data.

A computer network may be a physical network, including physical nodes connected by physical links. A physical node is any digital device. A physical node may be a function-specific hardware device, such as a hardware switch, a hardware router, a hardware firewall, and a hardware NAT. Additionally or alternatively, a physical node may be a generic machine that is configured to execute various virtual machines and/or applications performing respective functions. A physical link is a physical medium connecting two or more physical nodes. Examples of links include a coaxial cable, an unshielded twisted cable, a copper cable, and an optical fiber.

A computer network may be an overlay network. An overlay network is a logical network implemented on top of another network (such as, a physical network). Each node in an overlay network corresponds to a respective node in the underlying network. Hence, each node in an overlay network is associated with both an overlay address (to address to the overlay node) and an underlay address (to address the underlay node that implements the overlay node). An overlay node may be a digital device and/or a software process (such as, a virtual machine, an application instance, or a thread) A link that connects overlay nodes is implemented as a tunnel through the underlying network. The overlay nodes at either end of the tunnel treat the underlying multi-hop path between them as a single logical link. Tunneling is performed through encapsulation and decapsulation.

In an embodiment, a client may be local to and/or remote from a computer network. The client may access the computer network over other computer networks, such as a private network or the Internet. The client may communicate requests to the computer network using a communications protocol, such as Hypertext Transfer Protocol (HTTP). The requests are communicated through an interface, such as a client interface (such as a web browser), a program interface, or an application programming interface (API).

In an embodiment, a computer network provides connectivity between clients and network resources. Network resources include hardware and/or software configured to execute server processes. Examples of network resources include a processor, a data storage, a virtual machine, a container, and/or a software application. Network resources are shared amongst multiple clients. Clients request computing services from a computer network independently of each other. Network resources are dynamically assigned to the requests and/or clients on an on-demand basis. Network resources assigned to each request and/or client may be scaled up or down based on, for example, (a) the computing services requested by a particular client, (b) the aggregated computing services requested by a particular tenant, and/or (c) the aggregated computing services requested of the computer network. Such a computer network may be referred to as a "cloud network."

In an embodiment, a service provider provides a cloud network to one or more end users. Various service models may be implemented by the cloud network, including but not limited to Software-as-a-Service (SaaS), Platform-as-a-Service (PaaS), and Infrastructure-as-a-Service (IaaS). In SaaS, a service provider provides end users the capability to use the service provider's applications, which are executing on the network resources. In PaaS, the service provider provides end users the capability to deploy custom applications onto the network resources. The custom applications may be created using programming languages, libraries, services, and tools supported by the service provider. In IaaS, the service provider provides end users the capability to provision processing, storage, networks, and other fundamental computing resources provided by the network resources. Any arbitrary applications, including an operating system, may be deployed on the network resources.

In an embodiment, various deployment models may be implemented by a computer network, including but not limited to a private cloud, a public cloud, and a hybrid cloud. In a private cloud, network resources are provisioned for exclusive use by a particular group of one or more entities (the term "entity" as used herein refers to a corporation, organization, person, or other entity). The network resources may be local to and/or remote from the premises of the particular group of entities. In a public cloud, cloud resources are provisioned for multiple entities that are independent from each other (also referred to as "tenants" or "customers"). The computer network and the network resources thereof are accessed by clients corresponding to different tenants. Such a computer network may be referred to as a "multi-tenant computer network." Several tenants may use a same particular network resource at different times and/or at the same time. The network resources may be local to and/or remote from the premises of the tenants. In a hybrid cloud, a computer network comprises a private cloud and a public cloud. An interface between the private cloud and the public cloud allows for data and application portability. Data stored at the private cloud and data stored at the public cloud may be exchanged through the interface. Applications implemented at the private cloud and applications implemented at the public cloud may have dependencies on each other. A call from an application at the private cloud to an application at the public cloud (and vice versa) may be executed through the interface.

In an embodiment, tenants of a multi-tenant computer network are independent of each other. For example, a business or operation of one tenant may be separate from a business or operation of another tenant. Different tenants may demand different network requirements for the computer network. Examples of network requirements include processing speed, amount of data storage, security requirements, performance requirements, throughput requirements, latency requirements, resiliency requirements, Quality of Service (QoS) requirements, tenant isolation, and/or consistency. The same computer network may need to implement different network requirements demanded by different tenants.

In one or more embodiments, in a multi-tenant computer network, tenant isolation is implemented to ensure that the applications and/or data of different tenants are not shared with each other. Various tenant isolation approaches may be used.

In an embodiment, each tenant is associated with a tenant ID. Each network resource of the multi-tenant computer network is tagged with a tenant ID. A tenant is permitted access to a particular network resource only if the tenant and the particular network resources are associated with a same tenant ID.

In an embodiment, each tenant is associated with a tenant ID. Each application, implemented by the computer network, is tagged with a tenant ID. Additionally or alternatively, each data structure and/or dataset, stored by the computer network, is tagged with a tenant ID. A tenant is permitted access to a particular application, data structure, and/or dataset only if the tenant and the particular application, data structure, and/or dataset are associated with a same tenant ID.

As an example, each database implemented by a multi-tenant computer network may be tagged with a tenant ID. Only a tenant associated with the corresponding tenant ID may access data of a particular database. As another example, each entry in a database implemented by a multi-tenant computer network may be tagged with a tenant ID. Only a tenant associated with the corresponding tenant ID may access data of a particular entry. However, the database may be shared by multiple tenants.

In an embodiment, a subscription list indicates which tenants have authorization to access which applications. For each application, a list of tenant IDs of tenants authorized to access the application is stored. A tenant is permitted access to a particular application only if the tenant ID of the tenant is included in the subscription list corresponding to the particular application.

In an embodiment, network resources (such as digital devices, virtual machines, application instances, and threads) corresponding to different tenants are isolated to tenant-specific overlay networks maintained by the multi-tenant computer network. As an example, packets from any source device in a tenant overlay network may only be transmitted to other devices within the same tenant overlay network. Encapsulation tunnels are used to prohibit any transmissions from a source device on a tenant overlay network to devices in other tenant overlay networks. Specifically, the packets, received from the source device, are encapsulated within an outer packet. The outer packet is transmitted from a first encapsulation tunnel endpoint (in communication with the source device in the tenant overlay network) to a second encapsulation tunnel endpoint (in communication with the destination device in the tenant overlay network). The second encapsulation tunnel endpoint decapsulates the outer packet to obtain the original packet transmitted by the source device. The original packet is transmitted from the second encapsulation tunnel endpoint to the destination device in the same particular overlay network.

8. Miscellaneous; Extensions

Embodiments are directed to a system with one or more devices that include a hardware processor and that are configured to perform any of the operations described herein and/or recited in any of the claims below.

In an embodiment, a non-transitory computer readable storage medium comprises instructions which, when executed by one or more hardware processors, causes performance of any of the operations described herein and/or recited in any of the claims.

Any combination of the features and functionalities described herein may be used in accordance with one or more embodiments. In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

9. Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs), field programmable gate arrays (FPGAs), or network processing units (NPUs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, FPGAs, or NPUs with custom programming to accomplish the techniques. The special-purpose computing devices may be desktop computer systems, portable computer systems, handheld devices, networking devices or any other device that incorporates hard-wired and/or program logic to implement the techniques.

Figure 7:
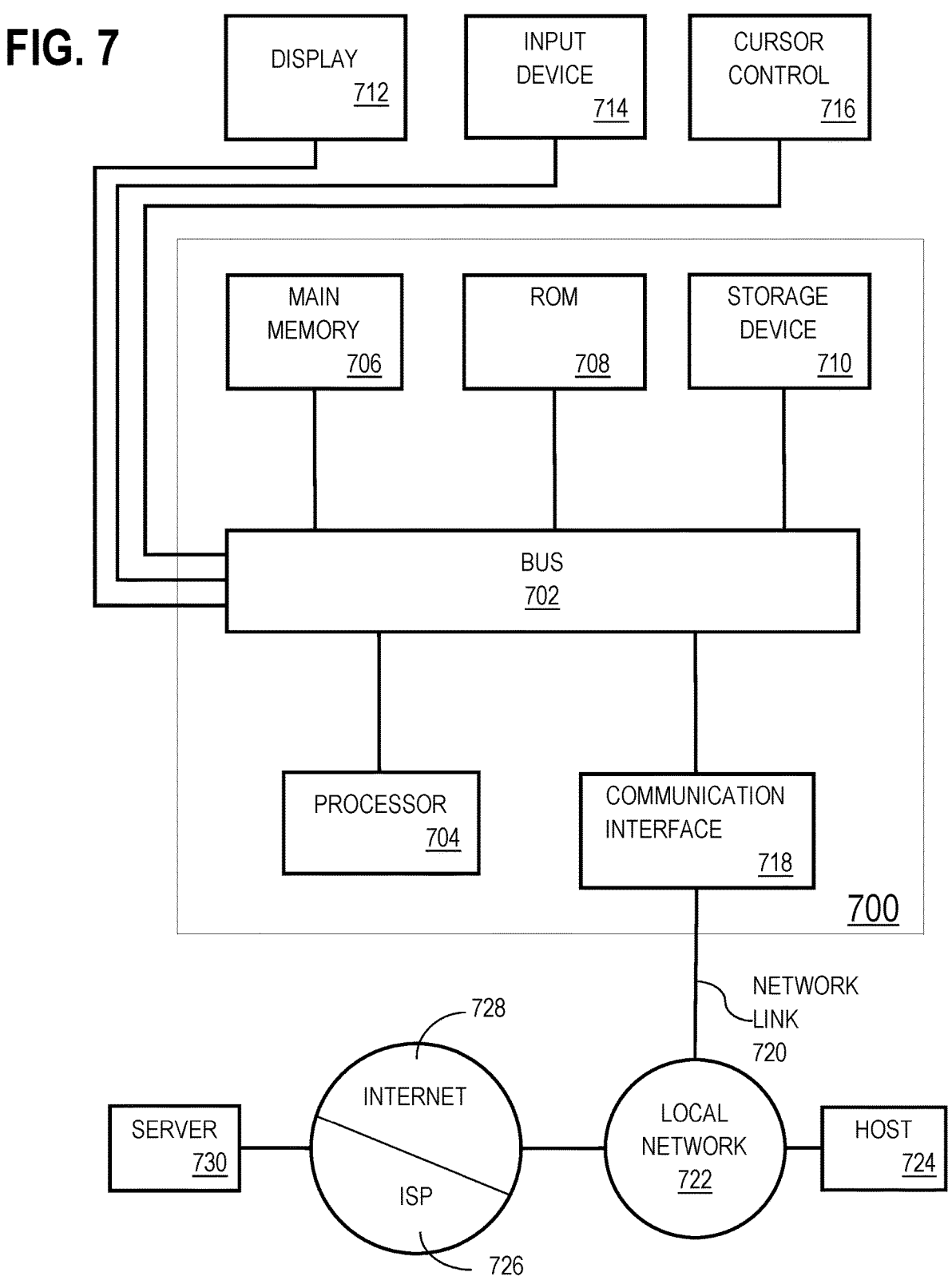
FIG. 7 shows a block diagram that illustrates a computer system in accordance with one or more embodiments.

For example, FIG. 7 is a block diagram that illustrates a computer system 700 upon which an embodiment of the invention may be implemented. Computer system 700 includes a bus 702 or other communication mechanism for communicating information, and a hardware processor 704 coupled with bus 702 for processing information. Hardware processor 704 may be, for example, a general purpose microprocessor.

Computer system 700 also includes a main memory 706, such as a random access memory (RAM) or other dynamic storage device, coupled to bus 702 for storing information and instructions to be executed by processor 704. Main memory 706 also may be used for storing temporary variables or other intermediate information during execution of instructions to be executed by processor 704. Such instructions, when stored in non-transitory storage media accessible to processor 704, render computer system 700 into a special-purpose machine that is customized to perform the operations specified in the instructions.

Computer system 700 further includes a read only memory (ROM) 708 or other static storage device coupled to bus 702 for storing static information and instructions for processor 704. A storage device 710, such as a magnetic disk or optical disk, is provided and coupled to bus 702 for storing information and instructions.

Computer system 700 may be coupled via bus 702 to a display 712, such as a cathode ray tube (CRT), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane.

Computer system 700 may implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor 704 executing one or more sequences of one or more instructions contained in main memory 706. Such instructions may be read into main memory 706 from another storage medium, such as storage device 710. Execution of the sequences of instructions contained in main memory 706 causes processor 704 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage device 710. Volatile media includes dynamic memory, such as main memory 706. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, content-addressable memory (CAM), and ternary content-addressable memory (TCAM).

Storage media is distinct from but may be used in conjunction with transmission media. Transmission media participates in transferring information between storage media. For example, transmission media includes coaxial cables, copper wire and fiber optics, including the wires that comprise bus 702. Transmission media can also take the form of acoustic or light waves, such as those generated during radio-wave and infra-red data communications.

Various forms of media may be involved in carrying one or more sequences of one or more instructions to processor 704 for execution. For example, the instructions may initially be carried on a magnetic disk or solid state drive of a remote computer. The remote computer can load the instructions into its dynamic memory and send the instructions over a telephone line using a modem. A modem local to computer system 700 can receive the data on the telephone line and use an infra-red transmitter to convert the data to an infra-red signal. An infra-red detector can receive the data carried in the infra-red signal and appropriate circuitry can place the data on bus 702. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card, cable modem, satellite modem, or a modem to provide a data communication connection to a corresponding type of telephone line. As another example, communication interface 718 may be a local area network (LAN) card to provide a data communication connection to a compatible LAN. Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the worldwide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are example forms of transmission media.

Computer system 700 can send messages and receive data, including program code, through the network(s), network link 720 and communication interface 718. In the Internet example, a server 730 might transmit a requested code for an application program through Internet 728, ISP 726, local network 722 and communication interface 718.

The received code may be executed by processor 704 as it is received, and/or stored in storage device 710, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. One or more non-transitory machine-readable media storing instructions which, when executed by one or more processors, cause performance of operations comprising:

training a machine learning model to determine whether users of wearable devices were asleep or awake at least by:

obtaining historical training data sets comprising:

a first historical training data set corresponding to a first period of time, wherein the first historical training data set comprises (a) a first set of user information corresponding to at least one user, collected by at least one wearable device, corresponding to the first period of time and (b) a first label indicating that the at least one user was asleep during the first period of time;

a second historical training data set corresponding to a second period of time, wherein the second historical training data set comprises (a) a second set of user information corresponding to the at least one user, collected by the at least one wearable device, corresponding to the second period of time and a second label indicating that the at least one user was awake during the second period of time;

training the machine learning model based on the historical training data sets;

executing the machine learning model in a wakefulness detection engine to determine whether a target user is awake or asleep, wherein the wakefulness detection engine is implemented in a first device, wherein the first device is at least one of: (a) a wearable device, and (b) a first remote device in communication with the wearable device;

detecting, using the wearable device during a third period of time, a third set of user information corresponding to the target user;

applying the machine learning model to the third set of user information, corresponding to the target user, to determine that the target user was asleep during the third period of time;

responsive to determining the target user was asleep during the third period of time: applying a first configuration for a first application running on a second device, wherein the second device comprises at least one of (a) the wearable device, and (b) a second remote device in communication with the wearable device;

detecting, by the first application, a first trigger event in the third period of time, wherein a first function, to be triggered by the first trigger event includes at least one of generating a light, generating a sound, and generating a vibration in the second device;

responsive to determining that the first application is in the first configuration, refraining from performing the first function mapped to the first trigger event in configuration data of the first application, even though the first trigger event for the first function was detected by the first application;

detecting, using the wearable device during a fourth period of time, a fourth set of user information corresponding to the target user;

applying the machine learning model to the fourth set of user information to determine that the target user was awake during the fourth period of time;

responsive to determining the target user was awake during the fourth period of time: applying a second configuration for the first application running on the second device;

detecting, by the first application, the first trigger event in the fourth period of time; and responsive to determining that the first application is in the second configuration, performing the first function mapped to the first trigger event in the configuration data of the first application.

2. The non-transitory machine-readable media of claim 1, wherein training the machine learning model based on the historical training data sets includes training the machine learning model to correlate sensor data collected by the at least one wearable device with whether the at least one user of the wearable device was asleep or awake, wherein the sensor data includes:

motion sensor data;

heart rate sensor data; and audio sensor data.

3. The non-transitory machine-readable media of claim 1, wherein the historical training data sets further comprise:

environmental information generated by one or more sensors in an environment in which the at least one wearable device is located.

4. The non-transitory machine-readable media of claim 1, wherein training the machine learning model based on the historical training data sets includes training the machine learning model to identify a daily pattern of wakefulness and sleep based on sensor data of the wearable device measured over a period spanning a plurality of days.

5. The non-transitory machine-readable media of claim 1, wherein training the machine learning model based on the historical training data sets includes training the machine learning model to correlate sensor data collected by the at least one wearable device with whether the at least one user of the wearable device was asleep or awake, wherein the sensor data includes:

motion sensor data;

heart rate sensor data; and audio sensor data;

wherein the historical training data sets further comprise:

environmental information generated by one or more sensors in an environment in which the at least one wearable device is located; and wherein training the machine learning model based on the historical training data sets includes training the machine learning model to identify a daily pattern of wakefulness and sleep based on the sensor data of the wearable device measured over a period spanning a plurality of days.

6. The non-transitory machine-readable media of claim 1, wherein the operations further comprise:

detecting, using the wearable device during a fifth period of time, a fifth set of user information corresponding to the target user;

applying the machine learning model to the fifth set of user information in real-time to determine that the target user is asleep during the fifth period of time;

responsive to determining the target user is asleep:

determining an elapsed sleep time that the target user has been asleep; and responsive to determining the elapsed sleep time meets a threshold:

triggering a second function of a third device to perform one of activating the second function and deactivating the second function.

7. The non-transitory machine-readable media of claim 1, wherein the operations further comprise:

receiving, by a cloud-based application, a first set of selections to apply the first configuration for the first application based on detecting a sleeping state of the target user;

based on the first set of selections, generating a first rule to apply the first configuration for the first application based on detecting the target user is asleep;

receiving, by a cloud-based application, a second selection to apply the second configuration for the first application based on detecting an awake state of the target user;

based on the second selection, generating a second rule to apply the second configuration for the first application based on detecting the target user is awake; and transmitting, by the cloud-based application, the first rule and the second rule to the second device.

8. The non-transitory machine-readable media of claim 7, wherein the operations further comprise:

receiving, by the cloud-based application, a third set of selections to apply a third configuration for a second application based on detecting a sleeping state of the target user;

based on the third set of selections, generating a third rule to apply a third configuration for the second application based on detecting the target user is asleep;

transmitting, by the cloud-based application, the third rule to the second device;

detecting, by the second application, a second trigger event in the third period of time, wherein a second function triggered by the second trigger event includes at least one of generating a light, generating a sound, and generating a vibration in the second device; and responsive to determining that the second application is in the third configuration, performing the second function associated with the second trigger event.

9. The non-transitory machine-readable media of claim 1, wherein the first application is a communications application, and wherein the first trigger event comprises the first application receiving a communication from a third device external to the wearable device.

10. The non-transitory machine-readable media of claim 1, wherein the operations further comprise:

responsive to determining the target user was asleep during the third period of time: applying a third configuration for a second application running on the second device;

detecting, by the second application, the first trigger event in the third period of time; and responsive to determining that the second application is in the third configuration, performing a second function associated with the first trigger event.

11. The non-transitory machine-readable media of claim 1, wherein the operations further comprise:

determining an elapsed time from when the first configuration was applied for the first application;

based on determining the elapsed time meets a threshold: applying a third configuration for the first application;

detecting, by the first application, the first trigger event in a fifth period of time; and responsive to determining that the first application is in the third configuration, performing the first function associated with the first trigger event.

12. The non-transitory machine-readable media of claim 1, wherein applying the first configuration for the first application running on the second device, responsive to determining the target user was asleep comprises:

changing a setting that maps the first trigger event to the first function from (a) enabling performance of the first function responsive to detecting the first trigger event to (b) disabling performance of the first function responsive to detecting the first trigger event.

13. The non-transitory machine-readable media of claim 1, wherein applying the first configuration for the first application running on the second device comprises storing a first value for a wakefulness setting, wherein the first value corresponds to an "asleep" state and a second value corresponds to an "awake" state, wherein determining that the first application is in the first configuration comprises determining the wakefulness setting stores the first value.

14. The non-transitory machine-readable media of claim 1, wherein the at least one user comprises the target user.

15. A method comprising:

training a machine learning model to determine whether users of wearable devices were asleep or awake at least by:

obtaining historical training data sets comprising:

a first historical training data set corresponding to a first period of time, wherein the first historical training data set comprises (a) a first set of user information corresponding to at least one user, collected by at least one wearable device, corresponding to the first period of time and (b) a first label indicating that the at least one user was asleep during the first period of time;

a second historical training data set corresponding to a second period of time, wherein the second historical training data set comprises (a) a second set of user information corresponding to the at least one user, collected by the at least one wearable device, corresponding to the second period of time and a second label indicating that the at least one user was awake during the second period of time;

training the machine learning model based on the historical training data sets;

executing the machine learning model in a wakefulness detection engine to determine whether a target user is awake or asleep, wherein the wakefulness detection engine is implemented in a first device, wherein the first device is at least one of: (a) a wearable device, and (b) a first remote device in communication with the wearable device;

detecting, using the wearable device during a third period of time, a third set of user information corresponding to the target user;

applying the machine learning model to the third set of user information, corresponding to the target user, to determine that the target user was asleep during the third period of time;

responsive to determining the target user was asleep during the third period of time: applying a first configuration for a first application running on a second device, wherein the second device comprises at least one of (a) the wearable device, and (b) a second remote device in communication with the wearable device;

detecting, by the first application, a first trigger event in the third period of time, wherein a first function, to be triggered by the first trigger event includes at least one of generating a light, generating a sound, and generating a vibration in the second device;

responsive to determining that the first application is in the first configuration, refraining from performing the first function mapped to the first trigger event in configuration data of the first application, even though the first trigger event for the first function was detected by the first application;

detecting, using the wearable device during a fourth period of time, a fourth set of user information corresponding to the target user;

applying the machine learning model to the fourth set of user information to determine that the target user was awake during the fourth period of time;

responsive to determining the target user was awake during the fourth period of time: applying a second configuration for the first application running on the second device;

detecting, by the first application, the first trigger event in the fourth period of time; and responsive to determining that the first application is in the second configuration, performing the first function mapped to the first trigger event in the configuration data of the first application.

16. The method of claim 15, wherein training the machine learning model based on the historical training data sets includes training the machine learning model to correlate sensor data collected by the at least one wearable device with whether the at least one user of the wearable device was asleep or awake, wherein the sensor data includes:

motion sensor data;

heart rate sensor data; and audio sensor data.

17. The method of claim 15, wherein the historical training data sets further comprise:

environmental information generated by one or more sensors in an environment in which the at least one wearable device is located.

18. The method of claim 15, wherein training the machine learning model based on the historical training data sets includes training the machine learning model to identify a daily pattern of wakefulness and sleep based on sensor data of the wearable device measured over a period spanning a plurality of days.

19. The method of claim 15, further comprising:

detecting, using the wearable device during a fifth period of time, a fifth set of user information corresponding to the target user;

applying the machine learning model to the fifth set of user information in real-time to determine that the target user is asleep during the fifth period of time;

responsive to determining the target user is asleep:

determining an elapsed sleep time that the target user has been asleep; and responsive to determining the elapsed sleep time meets a threshold:

triggering a second function of a third device to perform one of activating the second function and deactivating the second function.

20. The method of claim 15, further comprising:

receiving, by a cloud-based application, a first set of selections to apply the first configuration for the first application based on detecting a sleeping state of the target user;

based on the first set of selections, generating a first rule to apply the first configuration for the first application based on detecting the target user is asleep;

receiving, by a cloud-based application, a second selection to apply the second configuration for the first application based on detecting an awake state of the target user;

based on the second selection, generating a second rule to apply the second configuration for the first application based on detecting the target user is awake; and transmitting, by the cloud-based application, the first rule and the second rule to the second device.

21. The method of claim 20, further comprising:

receiving, by the cloud-based application, a third set of selections to apply a third configuration for a second application based on detecting a sleeping state of the target user;

based on the third set of selections, generating a third rule to apply a third configuration for the second application based on detecting the target user is asleep;

transmitting, by the cloud-based application, the third rule to the second device;

detecting, by the second application, a second trigger event in the third period of time, wherein a second function triggered by the second trigger event includes at least one of generating a light, generating a sound, and generating a vibration in the second device; and responsive to determining that the second application is in the third configuration, performing the second function associated with the second trigger event.

22. A system comprising:

at least one device including a hardware processor;

the system being configured to perform operations comprising:

training a machine learning model to determine whether users of wearable devices were asleep or awake at least by:

obtaining historical training data sets comprising:

a first historical training data set corresponding to a first period of time, wherein the first historical training data set comprises (a) a first set of user information corresponding to at least one user, collected by at least one wearable device, corresponding to the first period of time and (b) a first label indicating that the at least one user was asleep during the first period of time;

a second historical training data set corresponding to a second period of time, wherein the second historical training data set comprises (a) a second set of user information corresponding to the at least one user, collected by the at least one wearable device, corresponding to the second period of time and a second label indicating that the at least one user was awake during the second period of time;

training the machine learning model based on the historical training data sets;

executing the machine learning model in a wakefulness detection engine to determine whether a target user is awake or asleep, wherein the wakefulness detection engine is implemented in a first device, wherein the first device is at least one of: (a) a wearable device, and (b) a first remote device in communication with the wearable device;

detecting, using the wearable device during a third period of time, a third set of user information corresponding to the target user;

applying the machine learning model to the third set of user information, corresponding to the target user, to determine that the target user was asleep during the third period of time;

responsive to determining the target user was asleep during the third period of time: applying a first configuration for a first application running on a second device, wherein the second device comprises at least one of (a) the wearable device, and (b) a second remote device in communication with the wearable device;

detecting, by the first application, a first trigger event in the third period of time, wherein a first function, to be triggered by the first trigger event includes at least one of generating a light, generating a sound, and generating a vibration in the second device;

responsive to determining that the first application is in the first configuration, refraining from performing the first function mapped to the first trigger event in configuration data of the first application, even though the first trigger event for the first function was detected by the first application;

detecting, using the wearable device during a fourth period of time, a fourth set of user information corresponding to the target user;

applying the machine learning model to the fourth set of user information to determine that the target user was awake during the fourth period of time;

responsive to determining the target user was awake during the fourth period of time: applying a second configuration for the first application running on the second device;

detecting, by the first application, the first trigger event in the fourth period of time; and responsive to determining that the first application is in the second configuration, performing the first function mapped to the first trigger event in the configuration data of the first application.

23. The system of claim 22, wherein training the machine learning model based on the historical training data sets includes training the machine learning model to correlate sensor data collected by the at least one wearable device with whether the at least one user of the wearable device was asleep or awake, wherein the sensor data includes:

motion sensor data;

heart rate sensor data; and audio sensor data.

24. The system of claim 22, wherein the historical training data sets further comprise:

environmental information generated by one or more sensors in an environment in which the at least one wearable device is located.

25. The system of claim 22, wherein training the machine learning model based on the historical training data sets includes training the machine learning model to identify a daily pattern of wakefulness and sleep based on sensor data of the wearable device measured over a period spanning a plurality of days.

26. The system of claim 22, wherein the operations further comprise:

detecting, using the wearable device during a fifth period of time, a fifth set of user information corresponding to the target user;

applying the machine learning model to the fifth set of user information in real-time to determine that the target user is asleep during the fifth period of time;

responsive to determining the target user is asleep:

determining an elapsed sleep time that the target user has been asleep; and responsive to determining the elapsed sleep time meets a threshold:

triggering a second function of a third device to perform one of activating the second function and deactivating the second function.

* * * * *